United States Patent [19]

Arnost et al.

[11] Patent Number: 4,886,744

[45] Date of Patent: Dec. 12, 1989

[54] FLUORESCENT CONJUGATES AND BIOLOGICAL DIAGNOSTIC ASSAY SYSTEM

[75] Inventors: Michael J. Arnost, North Andover; Shai Inbar, Brookline; Frank A. Meneghini, Arlington; Paul S. Palumbo, West Newton; Stephen G. Stroud, Medford; Charles M. Zepp, Berlin, all of Mass.

[73] Assignee: Polaroid Corporation, Cambridge, Mass.

[21] Appl. No.: 850,123

[22] Filed: Apr. 10, 1986

Related U.S. Application Data

[63] Continuation-in-part of Ser. No. 727,126, Apr. 25, 1985, abandoned.

[51] Int. Cl.$^4$ .................. C12Q 1/68; G01N 33/533
[52] U.S. Cl. .................................. 435/6; 435/30; 435/34; 436/501; 436/512; 436/546; 436/800; 935/78; 548/468; 549/426
[58] Field of Search .............. 436/532, 546, 800, 501, 436/512; 435/6, 803, 30, 34; 935/78; 549/426; 548/468

[56] References Cited

U.S. PATENT DOCUMENTS

| | | | |
|---|---|---|---|
| 3,852,683 | 12/1974 | Webster et al. | 252/301.2 R |
| 4,220,450 | 9/1980 | Maggio | 435/7 |
| 4,238,195 | 12/1980 | Boguslaski et al. | 435/7 |
| 4,473,652 | 9/1984 | Okazaki et al. | 436/536 |
| 4,542,104 | 9/1985 | Stryer et al. | 436/536 |
| 4,555,396 | 11/1985 | Frank et al. | 424/3 |

*Primary Examiner*—Robert Benson
*Attorney, Agent, or Firm*—Gaetano D. Maccarone

[57] ABSTRACT

Fluorescent compounds which are conjugates of a biologically active moiety and an arylidene dye moiety. The compounds have a large Stokes shift and are useful in applications such as biological diagnostic elements.

12 Claims, No Drawings

FLUORESCENT CONJUGATES AND BIOLOGICAL DIAGNOSTIC ASSAY SYSTEM

CROSS-REFERENCE TO RELATED APPLICATIONS

This application is a continuation-in-part of prior copending application Ser. No. 727,126, filed April 25, 1985, abandoned.

BACKGROUND OF THE INVENTION

Various procedures are known in the biomedical art employing biologically active compounds containing a detectable signal-generating dye moiety which may, for example, be a moiety which emits electromagnetic radiation, e.g. a fluorescent, chemiluminescent or bioluminescent substance. The biologically active compound may, for example, be a DNA probe, e.g. a labeled DNA probe of the type used in detecting complimentary DNA sequences; an enzyme; enzyme inhibitor; antigen; antibody; hapten; etc.

In recent years, much attention has been focused upon labeled-reagent immunoassays for the detection of body fluid antigens, hormones, infectious agents, serum antibodies, and the like. Consequently, the patent literature is replete with disclosures of various assays involving a labeled-reagent reaction between antigens and antibodies to provide a detectable signal, e.g. a change in color, emission of electromagnetic radiation, etc. These assays can be said to involve an immunological interaction between a ligand and an antiligand, wherein at least one of the two reactants contains a substance or a precursor of a substance which can produce the detectable signal as a function of the immunological ligand-antiligand interaction.

One class of labels commonly used in such assays are fluorescent dyes or fluorophors. Both heterogeneous and homogeneous specific binding assays employing fluorescent labeled conjugates are well known and are reported in the patent literature. By way of illustrating the general state of the art with respect to the use of fluorescers as labels in specific binding assays, mention may be made of U.S. Pat. Nos. 3,992,631; 3,999,948; 4,020,151; 4,025,310; 4,036,946; 4,058,732; 4,115,699; 4,220,450; and 4,238,195.

In general, it can be said that fluorescent labels for use in these assays should exhibit the highest possible fluorescent efficiency, have a relatively long emission wavelength (above 500 nm), and be capable of being bound covalently to the liquid or antiligand without negatively affecting the conjugation properties.

In addition, the fluorescent labels should ideally have a high Stokes shift (energy difference between absorption and emission). A high Stokes shift is desirable as it reduces interference by scattered light and system fluorescent background. Assay systems relying upon energy transfer, e.g., from a chemiluminescent source to a fluorescent label to provide a detectable signal are described, for example, in the aforementioned U.S. Pat. No. 4,220,450.

The present invention relates to novel fluorescent conjugates and their use in biological diagnostic elements.

It is therefore an object of the invention to provide novel fluorescent compounds.

It is another object to provide novel fluorescent compounds which include a biologically active moiety and a dye moiety.

It is a further object to provide novel fluorescent compounds which include a substantially achromophoric moiety.

Still another object is to provide biological diagnostic elements which utilize such novel fluorescent compounds.

BRIEF SUMMARY OF THE INVENTION

These and other objects and advantages are accomplished in accordance with the invention by providing novel fluorescent compounds which include a biologically active moiety and a radical of a dye represented by the formula

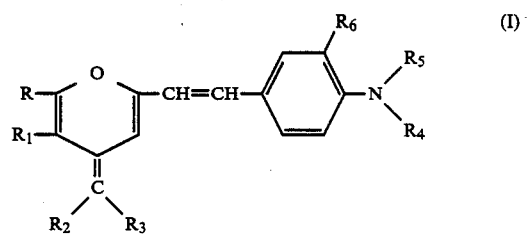

wherein R is alkyl, preferably having from 1 to 6 carbon atoms or a hydrophilic group; $R_1$ is hydrogen; or when R and $R_1$ are taken together they represent the carbon atoms necessary to form a six member benzene moiety thus, forming a benzopyran moiety. The benzene ring may be substituted at any of the available positions with substituents such as methoxy, or $EtO_2CCH_2O$—; or a divalent —OCH=CH— group may be attached to two of the carbon atoms of the benzene ring to form a further fused ring system;

$R_2$ and $R_3$ are each independently electron withdrawing groups such as —CN, —$COR_7$, —$COOR_8$ or phenyl substituted with electron withdrawing group(s) such as those described above; or when taken together with the carbon atom to which they are attached $R_2$ and $R_3$ represent a radical represented by

wherein X represents the nonmetallic atoms necessary to complete a five or six member carbocyclic or heterocyclic moiety including substituted rings and fused ring structures. A typical carbocyclic moiety is an indanedione represented by

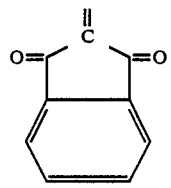

and a typical heterocyclic moiety is a radical of a barbituric acid represented by

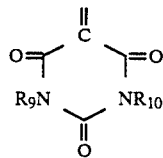

$R_4$ and $R_5$ are each independently alkyl, preferably having from 1 to 6 carbon atoms or a hydrophilic group, or $R_5$ when taken together with $R_6$ is $+CH_2\overline{)z}$;

$R_6$ is hydrogen;

$R_7$ is alkyl, preferably having from 1 to 6 carbon atoms, or aryl such as phenyl;

$R_8$ is alkyl, preferably having from 1 to 6 carbon atoms, aryl such as phenyl, or a hydrophilic group;

$R_9$ and $R_{10}$ each independently is hydrogen, alkyl, preferably having from 1 to 6 carbon atoms, or a hydrophilic group.

By "hydrophilic group" as used in the specification and claims herein, is meant a group which will improve the solubility of the molecule in water.

In a preferred embodiment at least one of R, $R_4$, $R_5$ or $R_8$ is a hydrophilic group; or $R_2$ or $R_3$ taken together form a five or six member carbocyclic or heterocyclic moiety as shown in Formula II. A common problem in assays of biological fluids is nonspecific absorption of the dye label to system components which distorts the assay results. The nonspecific binding is hydrophobic in nature in most instances. In order to minimize nonspecific binding it is desirable to render the dye molecule hydrophilic. This can be done by placing a hydrophilic group in at least one and preferably two positions on the molecule. Such an arrangement would reduce the exposed part of the hydrophobic dye molecule. Also, many dyes are known to aggregate in various solvents. The presence of one or more hydrophilic groups will minimize this phenomenon in water. The biological conjugates of the invention are useful in applications involving the testing of biological fluids such as plasma and serum and therefore the presence, in the conjugates, of one or more hydrophilic groups is preferred. In addition, the carbocyclic and heterocyclic moieties within Formula II can change the spectral properties of the compounds thus providing flexibility with respect to the absorption and emission maxima of the compounds.

Typical suitable hydrophilic groups which may be incorporated in the compounds of the invention include: carboxylic acids (—COOH); polyethers such as those which are represented by $+OCH_2CH_2\overline{)a}OEt$ where a is an integer of from 1 to 20, such as polyethylene oxide; polyalcohols which are represented by $-CH_2+CHOH\overline{)b}CH_2OH$ where b is an integer of from 1 to 20; primary, secondary or tertiary amines which are represented by $-NR_{11}R_{12}$ where $R_{11}$ and $R_{12}$ are each independently hydrogen, alkyl, preferably having from 1 to 6 carbon atoms, aryl such as phenyl or polyamines such as

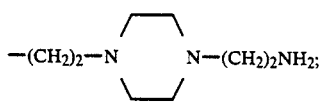

sulfonic acids (—SO$_3$H); phosphonic acids or esters which are represented by $+CH_2\overline{)c}PO(OR_{13})(OR_{14})$, where c is an integer of from 1 to 8 and $R_{13}$ and $R_{14}$ are each independently hydrogen, alkyl, preferably having from 1 to 6 carbon atoms, alkyl substituted with substituents such as carboxy or sulfo, aryl such as phenyl or substituted aryl; phosphates represented by $+CH_2\overline{)c}OPO(OH)_2$; phosphate esters represented by $+CH_2\overline{)c}OPO(OH)(OR_{15})$ where $R_{15}$ is alkyl, preferably having from 1 to 6 carbon atoms or aryl such as phenyl; phosphinic acids represented by $+CH_2\overline{)c}PO(OH)R_{16}$ where $R_{16}$ is alkyl, preferably having from 1 to 6 carbon atoms, boronic acids represented by $-R_{17}-B(OH)_2$ wherein $R_{17}$ is $+CH_2\overline{)c}$ or aryl such as phenyl; and borinic acids represented by $-R_{17}-B(OH)R_{16}$. As will be shown in detail, the compounds of the invention may include one or more of the same hydrophilic groups or they may include more than one different type of hydrophilic group.

The dye moiety shown in Formula I encompasses some known species which are described in U.S. Pat. No. 3,852,683 including, for example, 4-dicyanomethylene-2-methyl-6-p-dimethylaminostyryl -4H-pyran (DCM) which is represented by

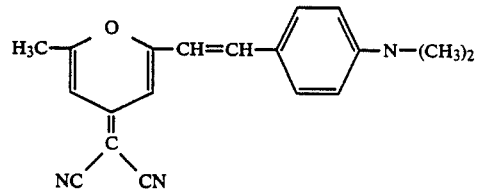

DCM is a highly fluorescent merocyanine dye having a large Stokes shift ($\lambda$ max abs.=481 nm; $\lambda$ fluoro. emiss.=644 nm; ethanol). The novel conjugates of the invention include a chromophore within Formula I together with a biologically active moiety which is attached to the dye chromophore through a divalent achromophoric linking group which can be represented by LINK. By the term "achromophoric moiety" is meant one which does not cause any appreciable shift in the spectral absorption characteristics of the dye moiety. Such a linkage should be non-conjugated.

Generally, therefore, the compounds of the invention have a dye moiety attached to the biologically active moiety through a divalent linking group represented by LINK wherein LINK is a substantially achromophoric moiety capable of reacting with a biologically active species to thereby link the chromophoric system of the dye to the biologically active moiety thus forming a labeled biological reagent.

The BIO moiety may be attached to the dye moiety of Formula I through any of the positions occupied by R, $R_2$, $R_3$, $R_4$, $R_5$, $R_9$ or $R_{10}$. Where R is alkyl such as methyl, for example, a divalent linking group may be used to attach a biologically active moiety to the dye moiety through this position. The labeled biological reagent produced in this manner can be represented by

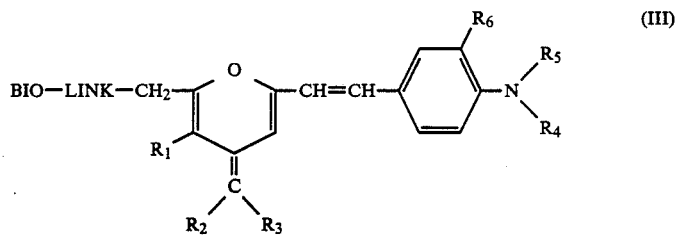
(III)

wherein BIO is a biologically active moiety, e.g. a DNA probe, an antibody, antigen, hapten, Fab fragment, etc.

Where the dye moiety is DCM the labeled biological reagents may be represented by

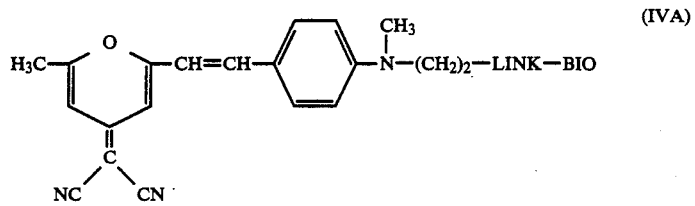
(IVA)

or

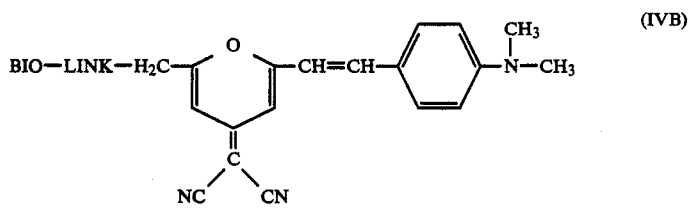
(IVB)

Functional groups which are useful as the LINK group together with the substituents of the BIO moiety with which they are reactable to provide the labeled conjugates of the invention such as those illustrated in Formulas III, IVA and IVB are:

| LINK | BIO |
| --- | --- |
| N—hydroxysuccinimide esters | amino groups (α-amino, lysine) |
| Imidoester | amino groups |
| Aldehydes | amino groups |
| Mixed anhydrides | nucleophilic groups |
| Isothiocyanates | nucleophilic groups |
| 2,4-dichloro-5-triazine | nucleophilic groups |
| Diazonium salts | tryptamine, histamine |
| Bromoacetyl | histamine, SH |
| Maleimido | SH |
| Activated disulfide bonds (e.g. 2-pyridyldisulfides) | SH |

Compounds which include a dye moiety within Formula I and a linking group may be illustrated, for example, by

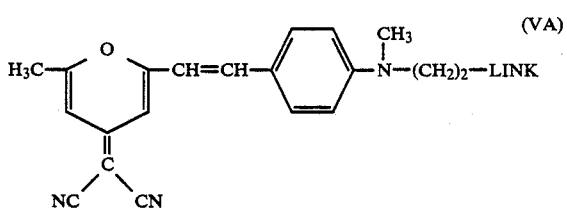
(VA)

-continued or

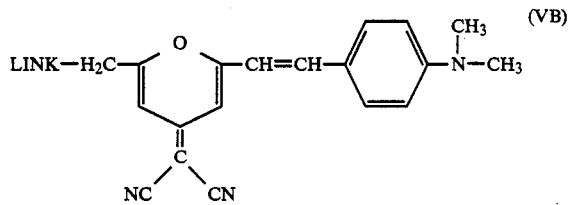
(VB)

Where a LINK group is attached to the dye moiety as illustrated in Formulas VA and VB, a preferred group of compounds is that wherein LINK is an N-hydroxysuccinimide ester represented by

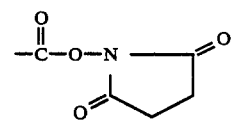

or a maleimido substituent represented by

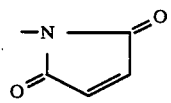

Accordingly, these compounds may be illustrated, for example, by

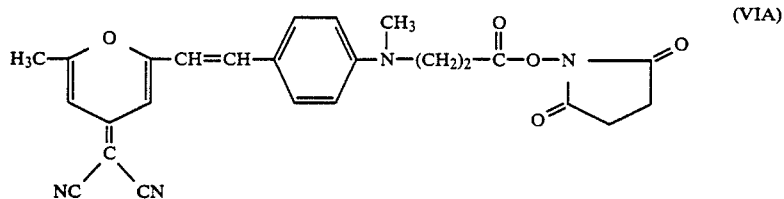

(VIA)

and

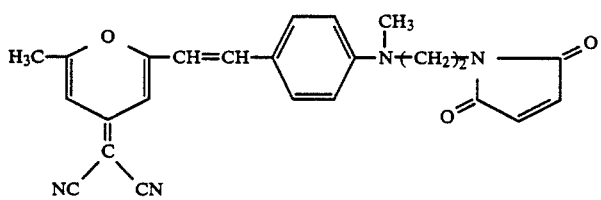

(VIB)

Of course it is apparent that when such compounds as are illustrated in Formulas VIA and VIB, are reacted with a biologically active moiety such as a protein, for example, the actual linking group which connects the dye moiety and the biologically active moiety will have a different structure. In the case of the N-hydroxysuccinimide ester, the biological conjugate could be expressed as

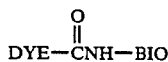

and as

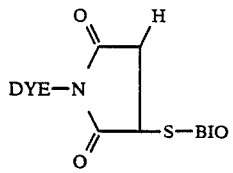

in the case of the maleimido substituent.

Many other linking groups may be used in the conjugates of the invention. For example, the hydrophilic groups mentioned above are substantially achromophoric and certain of these can be derivatized and utilized as suitable linking groups. For example, an —NH$_2$ group can be converted to an amide and the biologically active moiety attached to it, i.e., —NHCO—BIO. Further, in one embodiment a hydrophilic group may be attached to the linking moiety. For example, in the case of a primary amine, one of the hydrogen atoms can be converted to an amide and the biologically active moiety attached to it as described above, and the other hydrogen atom can be converted to a hydrophilic group such as —(CH$_2$)$_2$PO$_3$H$_2$. Thus it will be appreciated that the linking group, while serving as the means for attaching the dye moiety to the biologically active moiety, can also have a hydrophilic group attached to it. In addition, the linking group may also function as a hydrophilic group as, for example, in the case of DYE—NH—BIO and

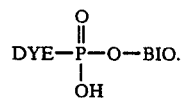

Since the labeled fluorescent compounds of the invention have a large Stokes shift they are useful in various applications including diagnostic assays which are based on an energy transfer mechanism to activate the fluorescent label.

DESCRIPTION OF THE PREFERRED EMBODIMENTS

A class of fluorescent labels is represented by

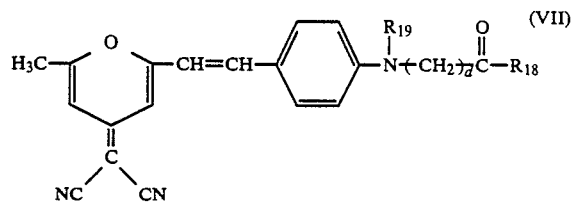

(VII)

wherein R$_{18}$ is —OH or

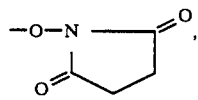

R$_{19}$ is alkyl having from 1 to 6 carbon atoms such as methyl or ethyl, and d is an integer of from 1 to 6.

A class of compounds according to the invention wherein a linking group is attached to the dye moiety is represented by

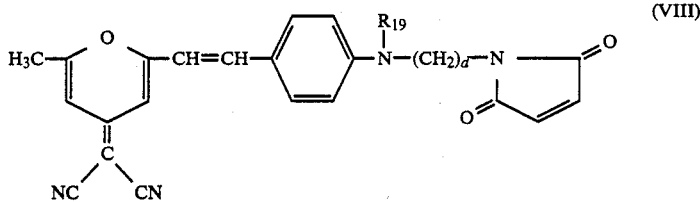

(VIII)

wherein d and $R_{19}$ are as previously described.

A class of dyes within Formula I is represented by

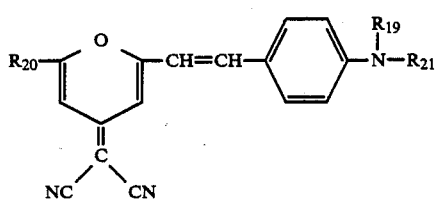

(IX)

where $R_{20}$ is alkyl, preferably having from 1 to 6 carbon atoms such as methyl or $-(CH_2)_d COOH$; $R_{21}$ is $-(CH_2)_d NR_{22}R_{23}$; $R_{22}$ and $R_{23}$ are each hydrogen or when taken together with the nitrogen atom to which they are attached form a maleimido group; and $R_{19}$ is as previously described.

Another class of dyes within Formula I is represented by moiety through a linkage which is attached to one of the available positions on the indoline ring.

A class of dyes within Formula I which has a carboxylic acid hydrophilic group and also may have a polyalcohol hydrophilic group is represented by

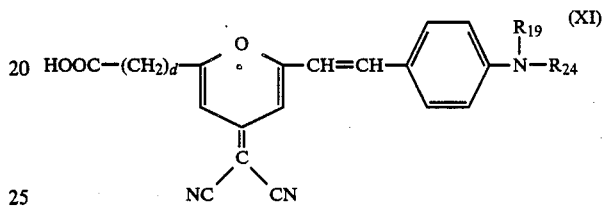

(XI)

where $R_{24}$ is alkyl, preferably having from 1 to 6 carbon atoms such as methyl or $-(CHOH)_3CH_2OH$; and d and $R_{19}$ are as previously defined.

A class of dyes within Formula I which has one polyalcohol hydrophilic group and a protected linking group is represented by

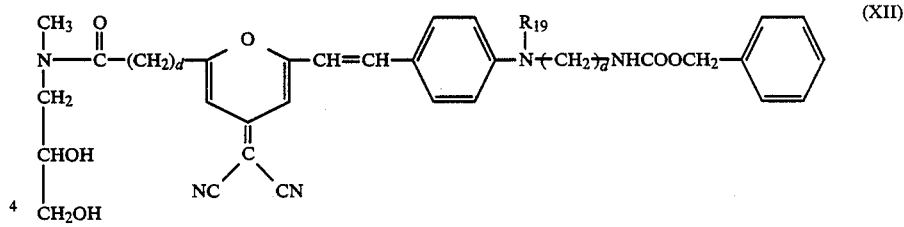

(XII)

wherein d and $R_{19}$ are as previously defined.

Another class of dyes which may have one or more hydrophilic groups and/or a linking group is represented by

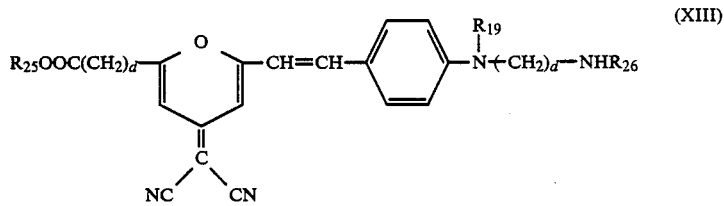

(XIII)

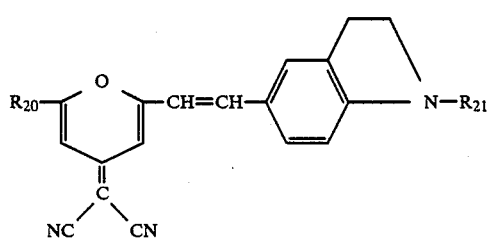

(X)

wherein $R_{20}$ and $R_{21}$ are as previously defined. It is possible to attach a biologically active group to the dye wherein $R_{25}$ is hydrogen or alkyl, preferably having from 1 to 6 carbon atoms such as methyl or ethyl; $R_{26}$ is $-(CH_2)_d-PO(OCH_2CH_3)_2$, $-(CH_2)_d CHOHCH_2OH$ or $-(CH_2)_d-PO_3H_2$; and $R_{19}$ and d are as previously defined.

A class of labels which has a phosphonic ester hydrophilic group and a maleimido linking group is represented by

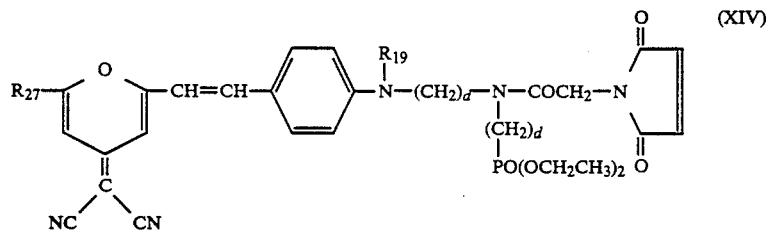

(XIV)

wherein $R_{27}$ is alkyl, preferably having from 1 to 6 carbon atoms such as methyl, etc. and d and $R_{19}$ are as previously defined.

A class of compounds within Formula I which includes two hydrophilic groups is represented by

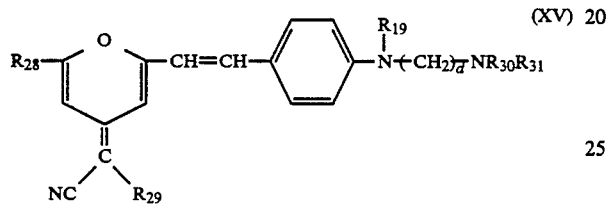 (XV)

wherein $R_{28}$ is alkyl, preferably having from 1 to 6 carbon atoms such as methyl, ethyl, etc., or —(CH$_2$)-$_d$COOH or —CON(CH$_3$)(CHOH)$_4$CH$_2$OH; $R_{29}$ is —CN, —COOCH$_2$CHOHCH$_2$OH or —COOCH$_2$PO$_3$H$_2$; $R_{30}$ is —(CH$_2$)$_d$(CHOH)$_3$CH$_2$OH, —(CH$_2$)$_d$—PO(OCH$_2$CH$_3$)$_2$ or —(CH$_2$)$_d$—PO$_3$H$_2$; $R_{31}$ is hydrogen, —COCH$_2$Br or

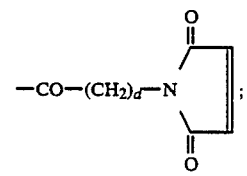

and d and $R_{19}$ are as previously described.

Specific compounds which include a dye moiety within Formula I and a linking group include:

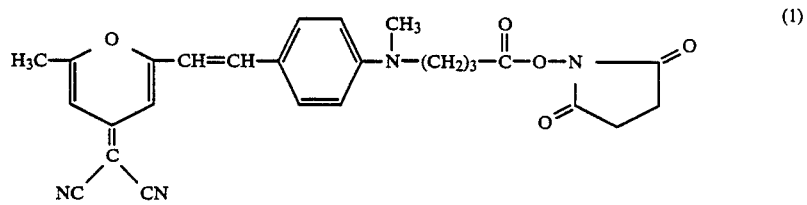 (1)

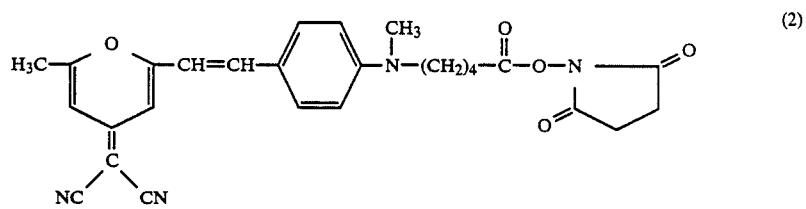 (2)

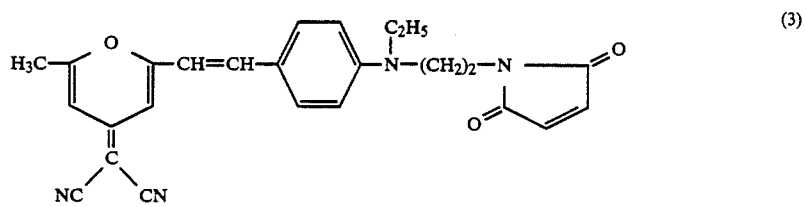 (3)

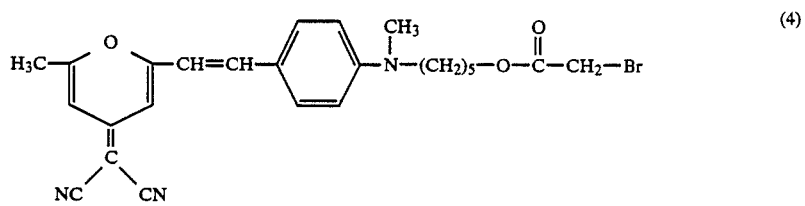 (4)

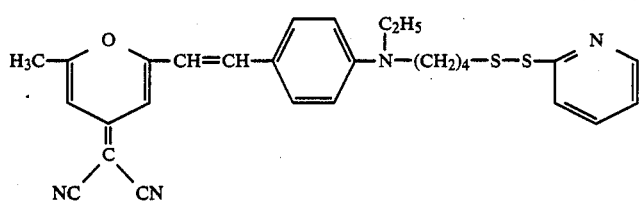 (5)
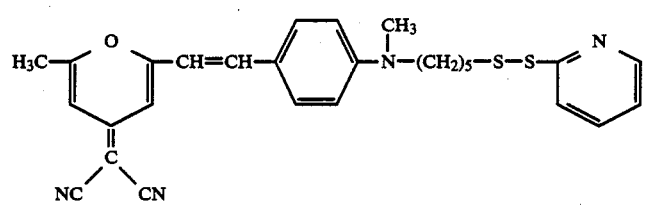 (6)
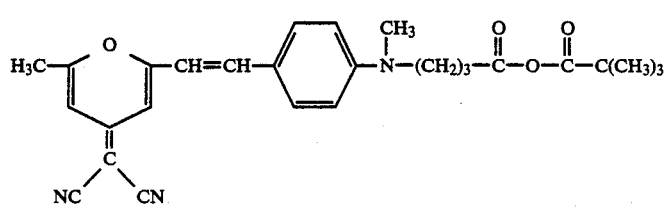 (7)
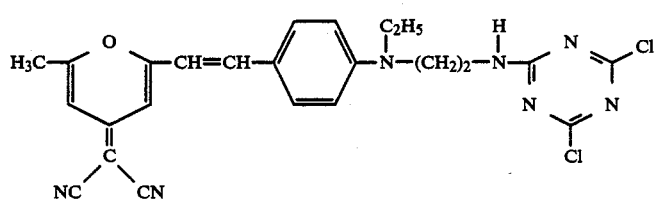 (8)
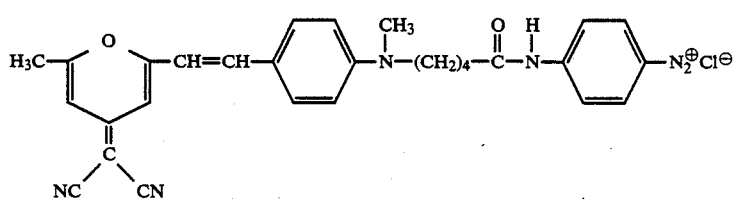 (9)
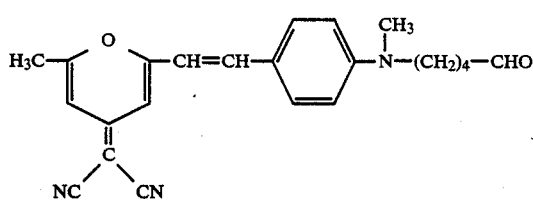 (10)
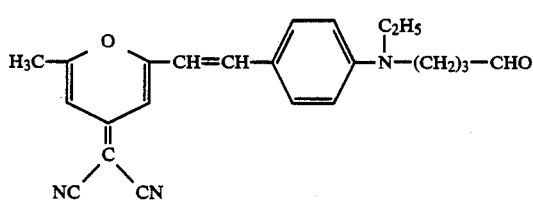 (11)
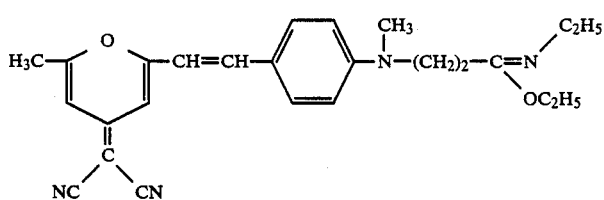 (12)

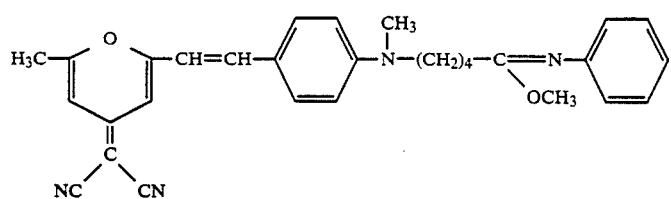

(13)

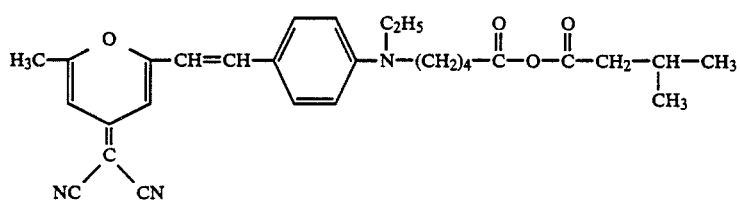

(14)

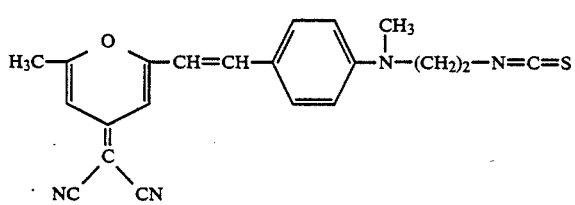

(15)

A class of labelled biological conjugates according to the invention is represented by

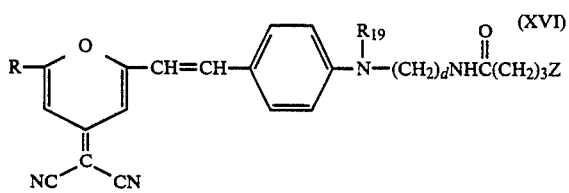

(XVI)

where Z is

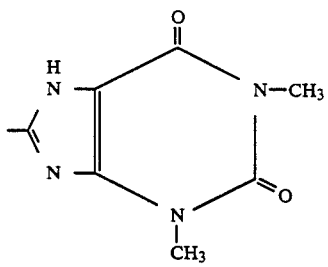

and R, $R_{19}$ and d are as previously described.

Another class of labelled biological conjugates according to the invention is represented by

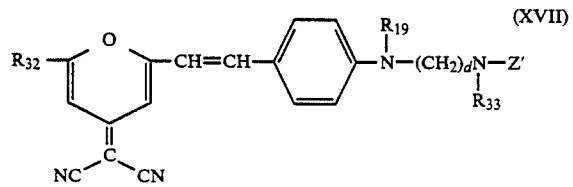

(XVII)

where $R_{32}$ is alkyl, preferably having from 1 to 6 carbon atoms such as methyl, ethyl, etc., —$(CH_2)_2COOH$, —$(CH_2)_2COOCH_2CH_3$ or —$(CH_2)_2CON(CH_3)CH_2(CHOH)_4CH_2OH$; $R_{33}$ is —$(CH_2)_2PO_3H_2$, —$CH_2(CHOH)_3CH_2OH$ or —$CH_2CHOHCH_2OH$; Z' is and $R_{19}$ is as previously defined. In these compounds the biological moiety, represented by Z', is linked to the dye moiety through a linking group which also has attached to it a hydrophilic group, represented by $R_{33}$.

Another class of labelled biological conjugates according to the invention is represented by (XVIII)

where $R_{34}$ is —$COOCH_2CHOHCH_2OH$ or —$COOCH_2PO_3H_2$, $R_{35}$ is —$CH_2(CHOH)_3CH_2OH$ or $(CH_2)_2PO_3H_2$; and R, $R_{19}$, Z' and d are as previously described.

Another class of labelled biological conjugates according to the invention is represented by

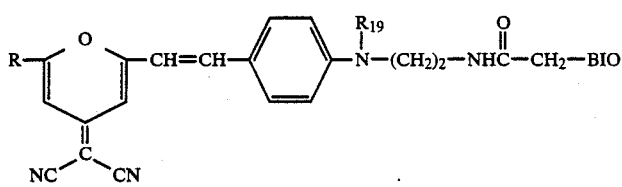

where R, $R_{19}$ and BIO are as previously defined.

The water solubility of certain labeled biological conjugates within Formula XVII was determined. Generally, a solution of the conjugate was formed, excess conjugate removed by filtration and the optical density of the filtrate obtained. The concentration of the conjugate was calculated from the optical density of the filtrate and the absorption coefficient ($\epsilon$) of the dye molecule. Compound XVIIA ($R_{32}$ is methyl; $R_{19}$ is ethyl; $R_{33}$ is —$(CH_2)_2PO_3H_2$; d is 2) compound XVIIB ($R_{32}$ is methyl, $R_{19}$ is ethyl; $R_{33}$ is —$CH_2(CHOH)_3CH_2OH$; d is 2) and compound XVIIC ($R_{32}$ is —$(CH_2)_2COOH$; $R_{19}$ is ethyl; $R_{33}$ is —$CH_2(CHOH)_3CH_2OH$; d is 2) had a solubility of $2.5 \times 10^{-4}$ mole/liter, $2.0 \times 10^{-5}$ mole/liter and $4 \times 10^{-4}$ mole/liter respectively.

Also the nonspecific absorption of compounds XVIIA and XVIIC to human serum albumin (HSA) was measured. The fluorescent yield of DCM which is bound to HSA differs substantially from that of DCM which is not bound to HSA. Accordingly, the change in fluorescent intensity as a function of different HSA concentration in a solution of constant DCM concentration was measured and the binding constant for the conjugate obtained by plotting the reciprocal of the relative quantum yield vs the reciprocal of the HSA concentration. The binding constant of compounds XVIIA and XVIIC was $2.5 \times 10^5$ mole$^{-1}$ and $1.5 \times 10^4$ mole$^{-1}$ respectively. A dye molecule within Formula I (R is methyl; $R_1$ is hydrogen, $R_2$ and $R_3$ are each —CN; $R_4$ is —$(CH_2)_2COOH$; $R_5$ is ethyl; and $R_6$ is hydrogen) exhibited a binding constant of $7 \times 10^5$ mole$^{-1}$.

These data illustrate that the presence of one or more hydrophilic groups in the dye moiety of the labeled conjugates typically increases the solubility and decreases the nonspecific binding of the conjugates.

The novel compounds of the invention generally may be synthesized by substitution reactions which are known to those skilled in the art of synthetic organic chemistry. Generally, the compounds may be prepared by condensing p-dialkylaminosubstituted benzaldehydes with 4-methylenepyrans as is described in U.S. Pat. No. 2,965,486. This general reaction scheme may be represented by the formula

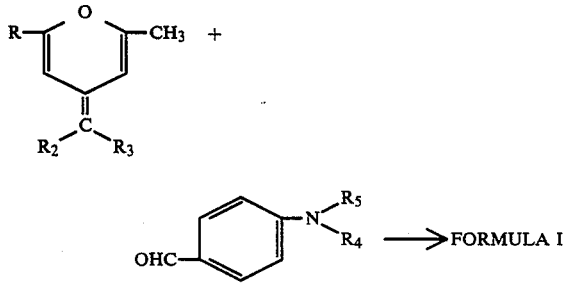

Consequently, the use of appropriately functionalized benzaldehyde and/or pyran analogs will provide the dye moiety with various appended functional groups.

For example, the synthesis of dye compounds containing carboxyethyl substituents at R requires the use of 2-methyl-6-carboxyethylsubstituted-$\gamma$-pyrones. These analogs can be prepared via alkylation of lithium dienolate of 2,6-dimethyl-$\gamma$-pyrone with bromoacetic acid derivatives according to the procedure described by A. B. Smith et al., J. Am. Chem. Soc., 103, 1501 (1982) and Tetrahedron Letters, 4193 (1978). In addition functional groups can be introduced at $R_4$ and $R_5$ at an early stage of the synthesis by way of reductive alkylations of N-methylaniline or N-ethyl-N-aminoethylaniline with substituted aldehydes. These aniline derivatives can then be formylated to provide the benzaldehydes used in the sequence to prepare the compounds which are functionalized at $R_4$ and $R_5$.

A linking substituent may be attached to the dye moiety by a reaction wherein the compound providing the linking substituent is reacted with N-methylamino styryl analog of DCM:

The preferred novel compounds of Formula (VIA) can be prepared by reacting 4-dicyanomethylene-2-methyl 6-p-(N-carboxyalkyl, N-alkyl)-aminostyryl-4-H-pyran (XX) with N-hydroxy-succinimide:

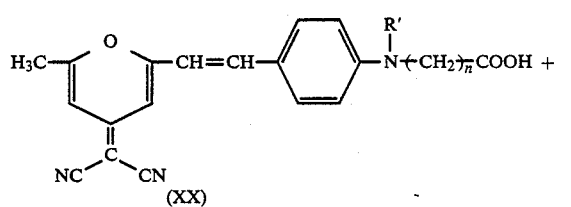

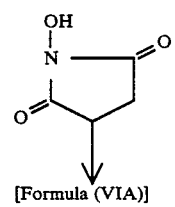

[Formula (VIA)]

If the pyran (XX) is not readily available, it may be obtained by reacting the carboxyalkylamino benzaldehyde analog (XXI) of the pyran with 4-dicyanomethylene-2,6-dimethyl-4H-pyran:

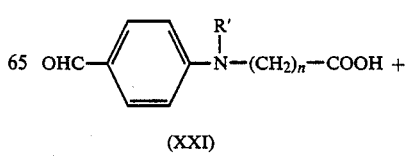

-continued

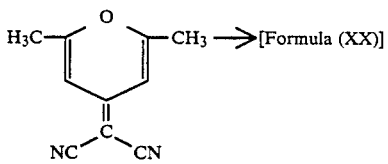

The carboxyalkylamino benzaldehyde (XXI) may be in turn derived from hydrolysis of the corresponding ester:

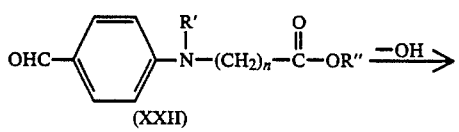

[Formula (XXI)]

If the ester (XXII) having the aldehyde substituent is not readily available, it may be obtained by formylation of the aminobenzene analog (XXIII):

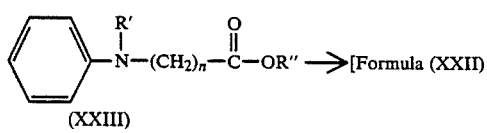

If desired, the alkyl substituent, R', on the nitrogen atom, may be obtained by alkylation of the secondary diamine analog of any of the above-mentioned compounds.

In some instances, as evidenced by Examples 1 and 2 which follow, it may be convenient to employ an N-phenyl cyclic amide as the starting material. Methoxylation of the keto moiety of the cyclic amide will in turn decyclize to form the secondary amine analog of the aminobenzene compound of Formula (XXIII), which may then be N-alkylated, as mentioned above, to form the intermediate (XXIII). This is a desirable procedure where the cyclic amide having the requisite number of nuclear carbon atoms for providing the —(CH2)$_n$- moiety, is readily available.

The novel compounds of Formula (VIB) may be obtained by the steps of: (a) reacting an amine of the formula:

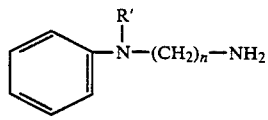

with phthalic anhydride to form a compound (XXIV) of the formula:

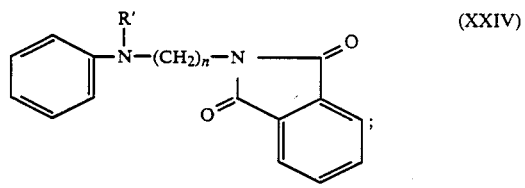

(b) formylating the above compound (XXIV) to obtain the corresponding aldehyde (XXV):

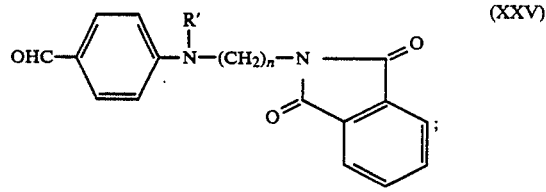

(c) reacting the aldehyde (XXV) with 4-dicyanomethylene-2,6-dimethyl-4-H-pyran to yield the pyran (XXVI):

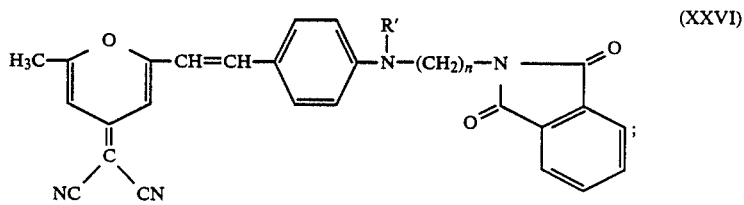

and then (d) removal of the phthalimide moiety and then forming the desired maleimide.

The labeled biological conjugates of the invention may be utilized in any of many applications such as for example, in diagnostic assays such as competitive binding assays or immunoassays or in immune response reactions employing labeled reagents. In a preferred embodiment the compounds are employed in drug monitoring applications such as for theophylline and digoxin. Thus, the compounds of the invention include labeled theophylline and labeled anti-digoxin. The particular assays in which the conjugates of the invention find utility are well known, for example, immunometric assays, competitive binding assays, etc., and therefore extensive discussion of such assays is not required here. In such known diagnostic tests or assays, a biological reaction or interaction results in the generation of a detectable signal. For instance, in typical immunoassay an analyte-containing sample comprising a body fluid such as serum or whole blood is applied to the surface of the diagnostic element. It then diffuses to a layer containing the labeled biologically active compound to produce an immunological reaction in accordance with the particular design or system of the diagnostic element and this reaction in turn generates a detectable signal signifying the presence of analyte in the sample fluid. The signal so generated may in less sophisticated systems provide only a qualitative determination of presence of analyte or it may provide in more sophisticated systems a semi-quantitative or quantitative measurement of the presence of the analyte. In such systems the biologically active compound containing the detectable signal-generating moiety may be a so-called label-protein conjugate, i.e., a protein such as an antigen, antibody or Fab fragment "labeled" with or containing the dye moiety.

The conjugates of the invention may also be used for fluorescent staining of cells. The cells may then be observed under a microscope, the presence of the fluorescent conjugate being diagnostic of the presence of a specific determinant site. Further, the conjugates may be used for the detection, separation or other application in a fluorescent activated cell sorter.

The invention will now be described further in detail with respect to specific preferred embodiments by way of examples, it being understood that these are intended to be illustrative only and the invention is not intended to be limited to the materials, conditions, process parameters, etc., which are recited therein.

EXAMPLE 1

(a) 500 mgs. (3.1 mmol) of N-phenyl pyrrolidone were dissolved in 10.0 ml. of chloroform and cooled to 0° C. 656 mg. (4.0 mmol) of methane trifluoromethane sulfonate were then added and the resulting mixture was warmed to 25° C. After stirring for about 16 hours, the mixture was poured into 10.0 ml. of anhydrous methanol and then stirred for 10 minutes. 5.0 ml. of a saturated solution of sodium bicarbonate was then added and the mixture was stirred for 10 minutes. The reaction mixture was then extracted with chloroform and dried over magnesium sulfate. Filtration and evaporation of the solvent provided 580 mg. or a 90% yield of the pure ester:

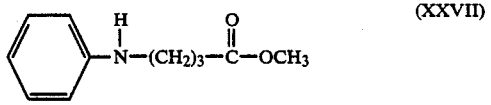

(XXVII)

(b) 6.0 g. (0.031 mol) of the above ester (XXVII) were added to 35 ml. of acetonitrile, followed by the addition of 5 ml. of 37% aqueous formaldehyde. 1.5 g. of sodium cyanoborohydride were added and the resulting mixture was then stirred at 25° C. for 30 minutes. The mixture was then poured into 75 ml. of water and acidified with acetic acid. It was then allowed to stand in an ice bath for 90 minutes and the pH was raised to pH 8 with 10% potassium carbonate solution. The mixture was then extracted with 2×100 ml ether, the combined organic layers washed with saturated sodium bicarbonate solution and then dried over magnesium sulfate. The solution was then filtered and the solvent evaporated to provide a quantitative yield of the colorless oil:

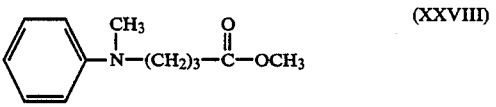

(XXVIII)

(c) 100 ml. of dimethyl formamide (DMF) was cooled to 0.° C. and 20.8 g. (0.135 mol) of POCl₃ were added dropwise. The mixture was then stirred for 15 minutes while warming to 25° C. An additional 100 ml. of DMF were added and the mixture was again cooled to 0° C. 15.0 g. (0.072 mol) of the ester (XXVIII) in 100 ml. DMF were then added dropwise over 30 minutes. The resulting mixture was warmed to 50° C. for 90 minutes. It was then cooled to 25° C. and poured into a cold solution of 100 g. of sodium acetate in 600 ml. of water. This mixture was then heated in a steam bath for 20 minutes, cooled in a water bath, and neutralized with 1M KOH. The precipitated oil was extracted with ether (3×300 ml.), dried over K₂CO₃, filtered and evaporated to provide 10 g. (84% yield) of the following aldehyde which was used without further purification:

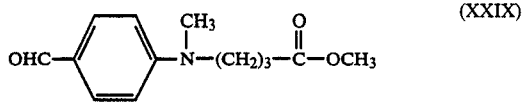

(XXIX)

(d) 5.0 g. (0.021 mol) of the above aldehyde (XXIX) were refluxed in 50 ml. of ethanol and 20 ml. of 1M KOH for about four hours. The mixture was then cooled and acidified with 1M HCl. The resulting white precipitate was filtered, washed with water and dried in vacuo to yield 4.6 g. of the following compound:

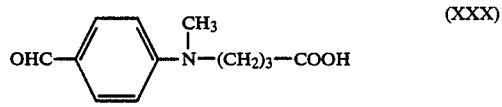

(XXX)

(e) 1.0 g. (4.5 mmol) of the previous product without further purification and 1.0 g. (5.9 mmol) of 4-dicyanomethylene-2,6-dimethyl-4-H-pyran were added to 40 ml. of DMF. 0.8 ml. of ethyl diisopropyl amine was then added and the mixture was refluxed under nitrogen for about four hours. The reaction mixture was then cooled and the DMF removed under high vacuum. The red-brown residue was purified by HPLC to provide 450 mg. (25% yield) of the pyran:

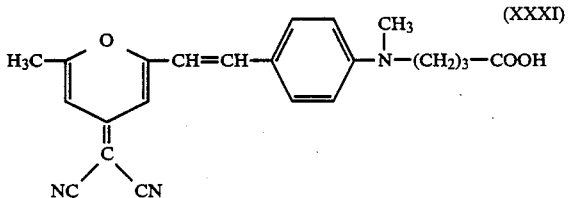

(XXXI)

(f) 100 mg. (0.26 mmol) of the pyran (XXXI) and 31 mg. (0.27 mmol) of N hydroxy succinimide were then mixed together in 3 ml. of dry DMF and cooled to −15° C. under nitrogen. 56 mg. (0.27 mmol) of dicyclohexyl carbodimide (DCC) were then added and the mixture was stirred at −15° C. for 90 minutes. It was then warmed to 25° C. and stirred for about 16 hours. The DMF was removed under high vacuum and the reddish residue dissolved in 10 ml. of acetone and filtered. The filtrate was evaporated and the reddish-brown residue purified by flash chromatography (silica, 10% CH₃CN/CH₂Cl₂) to provide a 75% yield of the fluorescent dye, Compound (1), a red powder, sol. in DMSO, acetone, acetonitrile; $\lambda_{max}$ abs. (H₂O)=471; $\lambda_{max}$ fluor. emiss. (H₂O)=615 nm.

As was mentioned earlier, the novel dyes of this invention exhibit essential the same spectral absorption characteristics as the "parent" compound, DCM. Comparison of the above data in Example 1 (471 and 615) with that of DCM (481 and 644) would seem to indicate to the contrary. However, the differences are due to the solvent employed in taking the readings. DCM is insoluble in water and is accordingly dissolved in an organic solvent to obtain the spectral characteristics. Compound 1 on the other hand, is water-soluble and was in a water solution.

EXAMPLE 2

The procedure described in Example 1 was repeated, substituting N-phenyl piperidone for the N-phenyl pyrrolidone in step (a) to provide a 95% yield of the fluorescent dye, of Compound 2.

The sequence of formation of reaction products in Example 2 accordingly was as follows:

(b) A dry 500 ml. flask was charged with 3 ml. of DMF and cooled to 0° C. under nitrogen. 4.9 g. (32 mmol) of POCl₃ were then added dropwise, the ice bath removed and the mixture stirred for 15 minutes. 50 ml. of DMF were then added and the mixture was cooled to 0° C. 9.0 g. (30.6 mmol) of compound (XXXII), above, in 50 ml. of DMF were added dropwise. After the addition was complete, the ice bath was removed and the mixture was warmed to 60° C. for 90 minutes. The mixture was cooled to 25° C. and poured into 250 ml. of water containing 30 g. of sodium acetate. A yellow

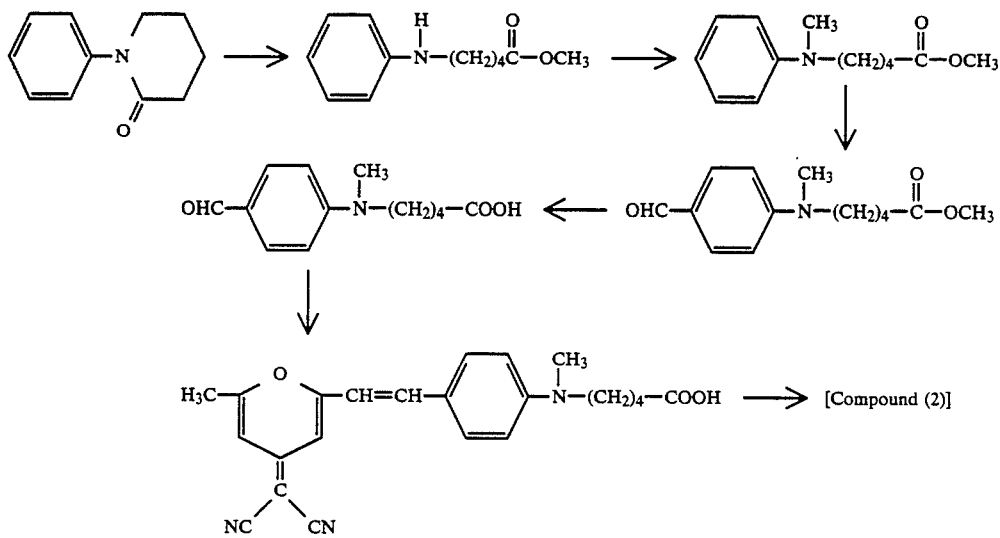

EXAMPLE 3

(a) A 500 ml. flask was charged with 300 ml. of methylene chloride, 16.5 g. (0.1 mol) of N-(2-aminoethyl)-N-ethyl aniline and 15.0 g. (0.1 mol) of phthalic anhydride. The reaction mixture was refluxed for 60 minutes and the solvent was then evaporated (aspirator). 200 ml. of acetic anhydride and 8 g. of sodium acetate were then added and the resulting mixture was refluxed for three hours, cooled and allowed to stand at room temperature overnight. The mixture was then filtered and the solvent was evaporated from the filtrate under vacuum. The solid residue was dissolved in methylene chloride and filtered through a silica gel plug. The solvent was evaporated and the yellow solid was recrystallized from hot ethanol to yield 17 g. (58% yield) of yellow crystals of the formula:

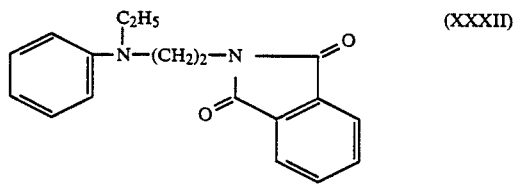

precipitate formed and was filtered off, washed with water and then dried. The crude yellow solid was recrystallized from 200 ml. of hot ethanol to provide 8 g. (81% yield) of yellow needles of the formula:

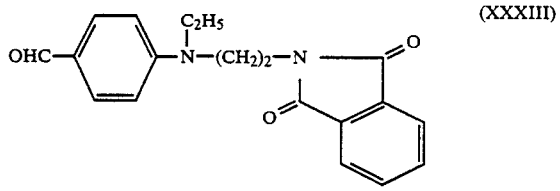

(c) 0.5 g. (1.55 mmol) of compound (XXXIII), above, 270 mg. (1.6 mmol) of 4-dicyanomethylene-2,6-dimethyl-4-H-pyran, and 0.15 ml. of diisopropyl ethyl amine were added to 7 ml. of DMF and refluxed under nitrogen for six hours. The DMF was removed under high vacuum, leaving a red-brown residue. This residue was purified by thin layer chromotography (methylene chloride) to provide a red powder of the formula;

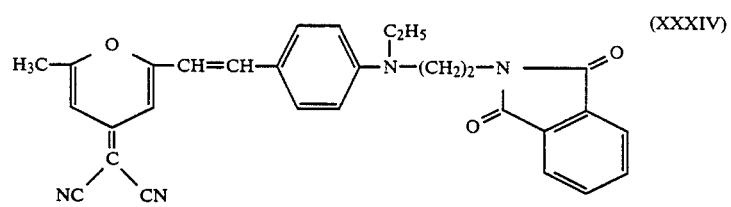

(d) 100 mg. (0.21 mmol) of Compound (XXXIV) above, were added to 10 ml. of absolute ethanol, followed by the addition of 8 mg. (0.25 mmol) of 95% hydrazine. The mixture was refluxed for 10 minutes and the solvent was removed by a nitrogen stream. The residue was taken up in methylene chloride and filtered. The filtrate was treated with 25 mg. (0.25 mmol) of maleic anhydride and stirred at 25° C. overnight. The methylene chloride was removed with nitrogen stream and 5 ml. of DMF and 103 mg. (0.5 mmol) of dicyclohexylcarbodiimide (DCC) were then added. The mixture was stirred at 25° C. for 25 hours, to provide the fluorescent dye, Compound 3, a red-brown powder; yield <95% sol. DMF;

EXAMPLE 4

1. 85×10$_{-7}$ mole Fab anti-HSA rabbit serum and 9.26×10$_{-7}$ mole of the fluorescent dye of formula (1) were added to a 0.1M HEPES buffer, pH 8.0 and the mixture was maintained at room temperature for twenty minutes, after which time the reaction was stopped by adding 1.33×10$_{-4}$ mole glycine. The resulting Fab-label conjugate was separated from the unconjugated fluorescent dye by gel filtration chromatography (cephadex G50). To insure the removal of non-specific bound fluorescent dye on the protein, the conjugate fraction was rechromatographed on Sephadex G560 and the second pooled fraction was extensively dialyzed. The composition of the conjugate ws determined by sepectroscopy. The Label/Fab ratio was 3:1.

EXAMPLE 5

Powdered sodium borohydride (7.0 g., 0.18 mole) was added slowly to a stirred solution of 1-methylindole (4.0 g., 0.03 mole) in 150 ml. of acetic acid which was cooled in an ice bath. The reaction mixture was then stirred at room temperature for 4 hours and at 60° C. for 3 hours. The reaction mixture was cooled to room temperature and slowly poured into a stirred solution of $Na_2CO_3$ (150 g.) in 1 liter of water. The mixture was transferred to a separatory funnel and the product extracted three times with 200 ml volumes of ethyl ether. The extractions were combined, washed with saline solution, dried over sodium sulfate and evaporated to yield a crude product which was distilled to give 2.8 g. (70% yield) of 1-methylindoline as a colorless oil, b.p. 72° C. (1.5 mm Hg).

$^1$H NMR (CDCl$_3$) δ 2.73 (s, 3H), 2.89 (t, 2H, J=7 Hz), 3.24 (t, 2H, J=7 Hz), 6.52 (m, 2H), 7.03 (m, 2H).

Phosphorus oxychloride (1.23 g., 0.0080 mole) was slowly added dropwise to 5 ml. of DMF which was cooled in an ice bath. The solution was stirred for 5 minutes and to it there was added dropwise a solution of 1-methylindoline (1.0 g., 0.0075 mole) in 2 ml. of DMF. The resulting mixture was stirred in the ice bath for 5 minutes, then at room temperature for 1 hour and finally at 80° C. for 2 hours. The reaction mixture was cooled to room temperature, slowly poured into water with stirring and extracted with ethyl ether. The crude oil was chromatographed on silica gel with 80/20 (v/v) $CH_2Cl_2$/EtOAc to yield 0.745 g. (62% yield) of 5-formyl-1-methylindoline as a yellow solid, m.p. 39°-41° C.

$^1$H NMR (CDCl$_3$) δ 2.79 (s, 3H), 2.89 (t, 2H, J=7), 3.43 (t, 2H, J=7), 6.25 (d, 1H, J=10), 7.46 (m, 2H), 9.56 (s. 1H).

The 5-formyl-1-methylindoline (0.500 g., 0.0031 mole) was combined with 4-dicyanomethylene-2,6-dimethyl-4-H-pyran (0.700 g., 0.0041 mole), DMF (7.5 ml.) and ethyldiisopropylamine (0.5 ml.) and the mixture refluxed for 8 hours under nitrogen. The dark reaction solution was cooled to room temperature and quenched into 100 ml. of stirred saline. The crude product was collected, washed with water and chromatographed (silica gel, $CH_2Cl_2$) to yield 250 mg. (26% yield) of a red solid

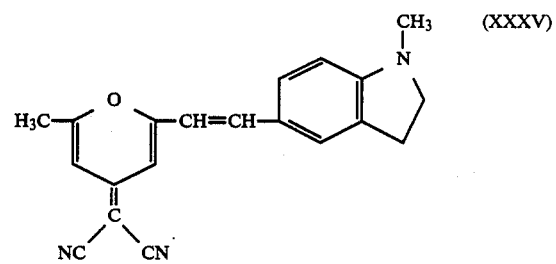

$^1$H NMR (CDCl$_3$) δ 2.31 (s, 3H), 2.79 (s, 3H), 2.92 (t, 2H), 3.42 (t, 2H), 6.2–6.5 (m, 4H), 7.1–7.4 (m, 3H).

Vis (meth. cell.): λ$_{max}$=477 nm (ε=53,250). Fluorescence emission (DMSO): 668 nm.

A solution of the previous product (25 mg., 0.08 mmole) in 5 ml. of $CH_2Cl_2$ was applied to a preparative silica gel TLC plate and allowed to dry for 3 hours. The plate was then eluted with $CH_2Cl_2$. A yellow band with slightly higher Rf than the previous product was scraped off and extracted. The extracts were evaporated to give 6.2 mg. (25% yield) of orange crystals

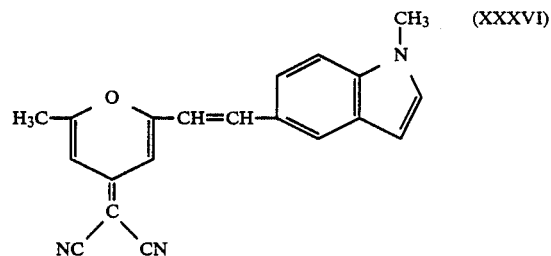

$^1$H NMR (CDCl$_3$) δ 2.38 (s, 3H), 3.83 (s, 3H), 6.4–6.7 (m, 4H), 7.0–7.8 (m,5H).

Vis (meth. cell.) λ$_{max}$=360 nm (ε=23,130); 428 nm (ε=13,640).

EXAMPLE 6

To a stirred solution of 1,1,1,3,3,3 hexamethyldisilazane (3.4 ml., 0.016 mole) in 60 ml. of dry THF, cooled under a dry nitrogen stream to −78° C., there was added 9.65 ml. (0.016 mole) of n-butyllithium (1.67M in hexane). After 1 hour, a solution of 2,6-dimethyl-γ-pyrone (2.0 g., 0.016 mole) in 45 ml. of dry THF was introduced via addition funnel over 30 minutes. The resulting bright yellow solution was stirred for 30 minutes and then treated dropwise via syringe with t-butyl bromoacetate (2.6 ml., 0.016 mole). The mixture was allowed to slowly warm to −10° C. and stand overnight. The resultant mixture was then transferred to a separatory funnel with ether, washed with 50 ml. of 1N HCl, 50 ml. of water and dried over magnesium sulfate. Evaporation of the solvent yielded 3.9 g. of product as an amber oil

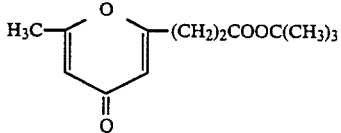

(XXXVII)

$^1$H NMR (CDCl$_3$) 1.45 (s, 9H), 2.2 (s,3H), 2.4–2.9 (m, 4H), 6.0 (bs, 2H).

TLC and NMR analysis of the oil showed it to be quite pure and it was used without further purification.

The pyrone ester, (XXXVII), (4.2 g., 0.018 mole) and malononitrile (1.28 g., 0.019 mole) were heated to reflux in 9 ml. of Ac$_2$O for 3 hours. The pure product was obtained by evaporation under high vacuum followed by silica gel chromatography (CH$_2$Cl$_2$) and recrystallization from hexane to give pale yellow needles

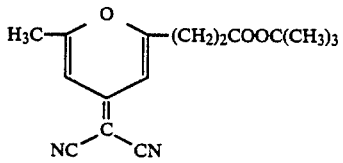

(XXXVIII)

$^1$H NMR (CDCl$_3$) δ 1.45 (s, 9H), 2.3 (s, 3H), 2.45–2.95 (m, 4H), 6.5 (s, 2H).

A room temperature solution of the dicyanomethylene pyran, (XXXVIII), (103 mg., 0.36 mmole in 2 ml. CH$_2$Cl$_2$ was treated with 0.5 ml. of trifluoroacetic acid and the resultant mixture stirred under argon for 5 hours. Evaporation to dryness quantitatively gave a tan solid

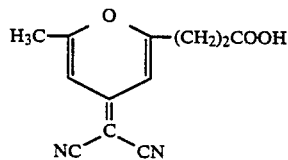

(XXXIX)

$^1$H NMR (d$_4$-methanol/CDCl$_3$) δ2.34 (s, 9H), 2.55–3.0 (m, 4H), 3.0 (s, 3H), 6.55 (bs, 2H).

EXAMPLE 7

A mixture of N-methylaniline (3.6 ml., 0.033 mole) and D-(−)-ribose (5.0 g., 0.033 mole) in 100 ml. of absolute ethanol was refluxed under argon for 6 hours. After removal of solvent under vacuum the resulting amber syrup was redissolved in 100 ml. of absolute ethanol and treated with sodium cyanoborohydride (2.07 g., 0.033 mole). The mixture was stirred at room temperature and 2N HCl-EtOH anhydrous solution added so as to maintain a pH of about 5–6 (bromocresol indicator). After 1 hour the solvent was removed on the rotary evaporator and the resulting residue cautiously treated with excess HCl-EtOH anhydrous solution and again evaporated under vacuum. The process was repeated three times. The residue was again taken in 100 ml. of absolute ethanol, treated with K$_2$CO$_3$ (1 g.) for 3 hours followed by suction filtration and evaporation of the filtrate. The crude product was dissolved in pyridine (250 ml.), treated with acetic anhydride (31 ml., 0.33 mole) and allowed to stand at room temperature overnight. Volatiles were removed under high vacuum and the product purified by chromatography on silica gel (1% MeOH in CH$_2$Cl$_2$). The product

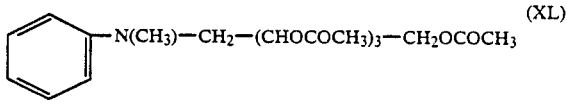

(XL)

eluted as the least polar band giving 1.12 g. (9% yield).

$^1$H NMR (CDCl$_3$) δ 1.85 (s, 3H), 2.05 (bs, 6H), 2.15 (s, 3H), 2.9 (s, 3H), 3.3–3.65 (m, 2H), 4.1–4.45 (m, 2H), 5.2–5.5 (m, 3H), 6.6–6.75 (m, 3H), 7.1–7.3 (m, 2H).

Phosphorus oxychloride (0.28 ml., 0.0030 mole) was added dropwise to 0.7 ml. (0.0089 mole) DMF with stirring. After one half hour a solution of the previous product, (XL), (1.1 g. 0.0027 mole) in 3 ml. DMF was introduced and the resultant mixture stirred at room temperature for 1½ hours and then at 60° C. for 3 hours. The cooled solution was quenched with several ml of water and then extracted twice with methylene chloride. The pure product was obtained via chromatography on silica gel (1% MeOH in CH$_2$Cl$_2$) to give 0.36 g. (30% yield) of

(XLI)

M$^+$(437).

$^1$H NMR (CDCl$_3$) δ 1.84 (s, 3H), 2.05 s, 3H), 2.13 (bs, 6H), 3.0 (s, 3H), 3.4–3.8 (m, 2H), 4.1–4.45 (m, 2H), 5.2–5.4 (m, 3H), 6.7 (d, J=10 Hz, 2H), 7.7 (d, J=10 Hz, 2H), 9.7 (s, 1H).

EXAMPLE 8

A compound represented by

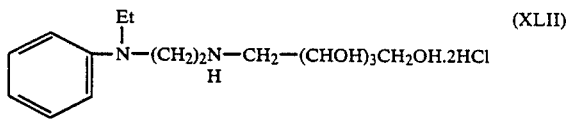

(XLII)

was prepared by a modification of the aminoalkylation procedure described for compound (XL) in Example 7. Accordingly, aminoethyl ethylaniline (2.0 g., 0.0122 mole) and D-(−)-ribose (1.84 g., 0.0123 mole) were combined and stirred at room temperature under argon overnight. Reduction with sodium cyanoborohydride (0.78 g., 0.0123 mole) in acidic EtOH followed by the typical collection procedure gave a crude syrup. The crude product was purified by chromatography on silica gel (5% acetic acid, 10% methanol in methylene chloride). The bis-HCl salt was generated in 20 ml. of absolute methanol and precipitated into 200 ml. of ether giving 1.52 g. (33% yield) of compound (XLII) as a hygroscopic solid; M$^+$(298; free base).

$^1$H NMR (d$_5$ pyridine, CDCl$_3$) δ 1.15 (t, J=7 Hz, 3H), 3.2–4.0 (m, 13H), 5.0 (bs, exchangables), 6.7 –7.1 (m, 3H), 7.2–7.55 (m, 2H).

To a stirred solution of 0.65 g. (0.0024 mole) of heating time was extended to an overnight period. An intermediate benzaldehyde compound

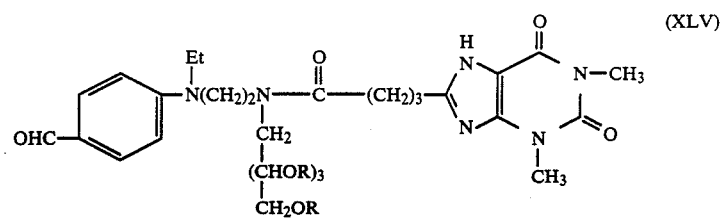

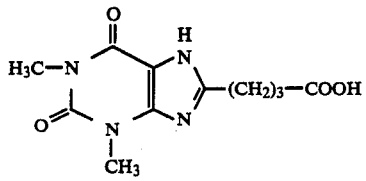

and triethylamine (1.05 ml., 0.0075 mole) in 12 ml. of DMF at 5° C. there was added 1,1,1-trimethylacetyl chloride (0.31 ml., 0.00255 mole). The resulting milky white suspension was stirred for 1 hour and then treated dropwise with a mixture of compound (XLII) and 0.35 ml. (0.00255 mole) triethylamine in 30 ml. of DMF. Stirring was continued at 5° C. for 30 minutes and then at room temperature for 1 hour. After evaporation under high vacuum the intermediate was chromatographed on silica gel (10% MeOH in $CH_2Cl_2$) to give a crystalline polyalcohol wherein R is —$COCH_3$, was obtained. The intermediate was chromatographed on silica gel (3% MeOH in $CH_2Cl_2$) and the resulting solid foam taken up in methanol, treated with 20 equivalents of triethylamine and refluxed for 7 hours. Evaporation under high vacuum gave a pale yellow solid, (XLV wherein R is hydrogen) in 49% overall yield, M+(575).

$^1H$ NMR was complex but consistent with the structure of the compound.

EXAMPLE 9

A mixture of compound (XLI) (0.355 g, 0.0008 mole) compound (XXXVIII) (0.23 g., 0.0008 mole) and 8 μl (0.1 equiv.) piperidine in 4 ml. of pyridine was refluxed overnight. The volatiles were removed under high vacuum and the resulting residue chromatographed on silica gel (1% MeOH in $CH_2Cl_2$) to give 0.17 g. (30% yield) of compound

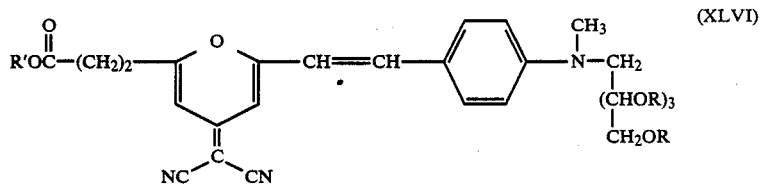

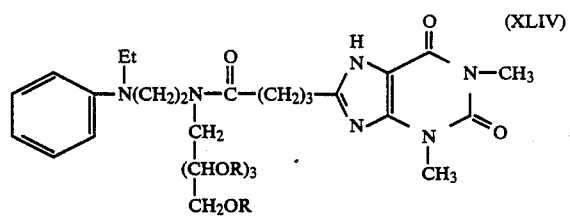

where R is hydrogen. The polyalcohol was taken up in 20 ml. of pyridine, treated with acetic anhydride (2.3 ml., 0.0242 mole) and allowed to stand at room temperature for 2 days. Volatiles were removed under high vacuum, the resulting residue taken up in ether, washed with water, dried and evaporated. Chromatography on silica gel (2–5% MeOH in $CH_2Cl_2$) gave 1.0 g. (56% yield) of a solid foam, (XLIV) where R is —$COCH_3$, M+(546).

$^1H$ NMR was complex but consistent with the structure of the product.

The previous polyalcohol intermediate (XLIV wherein R is —$COCH_3$) was formylated by the procedure described in the synthesis of compound (XLI). The where R is —$COCH_3$ and R' is t-butyl.

The compound was dissolved in 3 ml of $CH_2Cl_2$, treated with 2 ml. of trifluoroacetic acid and stirred at room temperature for 4 hours. The mixture was evaporated to dryness and the resulting residue chromatographed on silica gel (5% MeOH in $CH_2Cl_2$) to give a compound (XLVI, where R is —$COCH_3$ and R' is H) in 90% yield. Removal of the acetyl protecting groups was accomplished in quantitative yield by treating compound (XLVI, R is —$COCH_3$, R' is H) with catalytic sodium methoxide in methanol. After chromatography on silica gel (5% HOAc, 10% MeOH in $CH_2Cl_2$) a compound was obtained (XLVI, R=R'=H), as an orange solid with good fluorescence, M+ (481).

$^1H$ NMR was complex but consistent with the structure of the compound.

EXAMPLE 10

A mixture of the pale yellow solid of Example 8 (XLV, R is H) 71 mg. 0.124 mmole), compound (XXXIX) (28 mg., 0.124 mmole) and 1.2 μl (0.1 equiv.) piperidine in 2 ml of pyridine was refluxed with under argon overnight. The residue obtained upon evaporation of solvent was chromatographed on silica gel (5% AcOH, 10% MeOH in $CH_2Cl_2$) to give 22 mg. (23% yield) of an orange solid

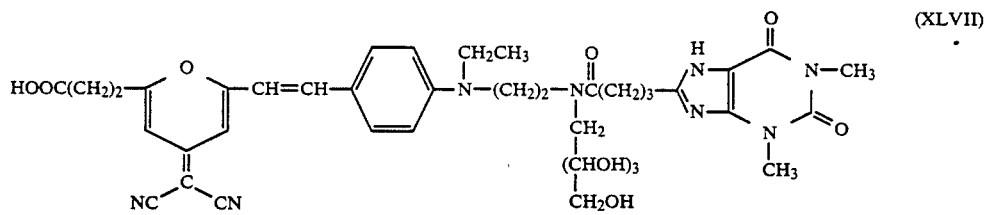

M+ (787).

$^1$H NMR was complex but consistent with the structure of the compound.

EXAMPLE 11

A mixture of 2(2'-carboethoxy)ethyl-6-methyl-4-dicyanomethylene pyran (200 mg., 0.77 mmole), pyridine (5 ml.), piperidine (100 μl) and p-(N-carbobenzyloxyaminoethyl-N-methylamino) benzaldehyde (242 mg., 0.77 mmole) was refluxed under nitrogen for 6 hours. The solvent was removed by evaporation under a nitrogen stream and the residue purified by column chromatography (2% MeOH in CHCl₃) to give 240 mg. (56% yield) of

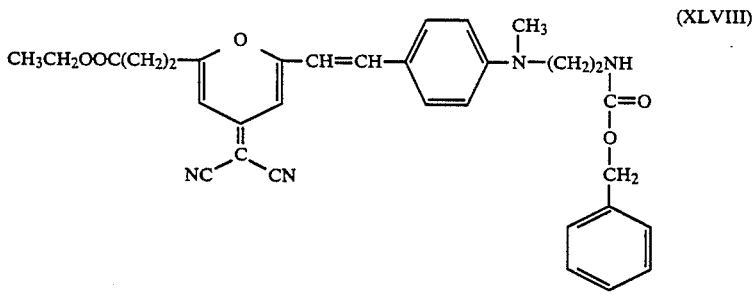

A mixture of (XLVIII) (230 mg., 0.4 mmole) and 5 ml. of saturated HBr/HOAc was stirred for 1½ hours, ether (50 ml.) added and the liquid layer decanted from the precipitated solid. The solid was washed with 50 ml. of ether, filtered and quickly dried under high vacuum to give the HBr salt of the free amine which was taken on to the next step without further purification.

Acetaldehyde diethyl phosphonate was added to a mixture of the amine HBr salt (approx. 0.7 mmole), NaHCO₃ (200 mg.) and 10 ml. of methanol and the mixture stirred under nitrogen at 25° C. for 17 hours. The reaction mixture was then centrifuged and the supernatent liquid decanted off. Sodium cyanoborohydride (440 mg., 7 mmole) was added to the liquid and the mixture stirred for 30 minutes at 25° C. Subsequently, 6 drops of conc. HCl were added over a 1½ hour period. The methanol was removed by evaporation and another 10 ml. of methanol added and then removed by evaporation. This procedure was repeated two more times and the resulting residue purified by column chromatography (8% MeOH in CH₂Cl₂) to give 141 mg. (35% yield) of a red powder

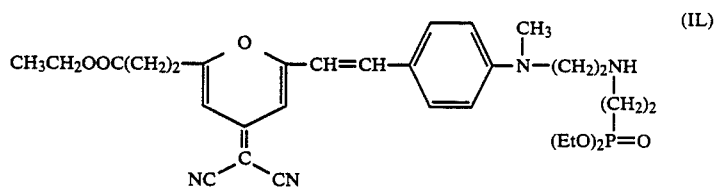

Theophylline-8-butyric acid (256 mg., 0.96 mmole) was added to a mixture of 8 ml. of dry DMF and triethylamine (75 mg., 0.96 mmole). The mixture was cooled to 0° C. under nitrogen with stirring and trimethylacetyl chloride (120 mg., 0.96 mmole) was added dropwise. After stirring for 1 hour at 0° C. a solution of compound 11B (140 mg., 0.24 mmole) in 2 ml. of DMF containing approximately 5 mg. of dimethylaminopyridine was added, the mixture warmed to 60° C. and stirred for an additional 2 hours. The solvent was removed with a nitrogen stream and the residue purified by chromatography (8% isopropanol in CHCl₃) to give 175 mg. (88% yield) of

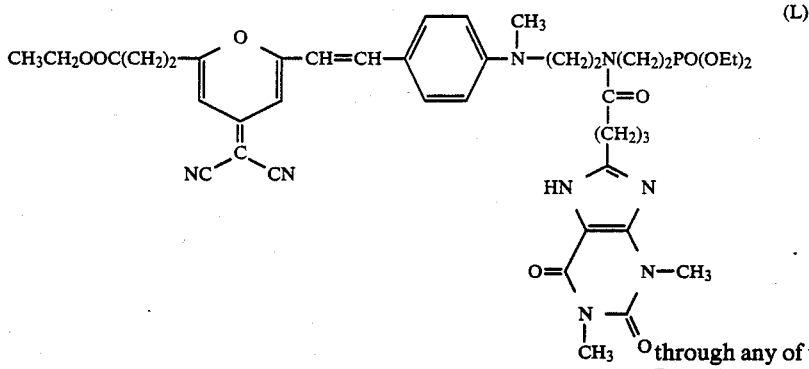

(L)

Although the invention has been described with respect to various specific preferred embodiments it is not intended to be limited thereto but rather those skilled in the art will recognize that variations and modifications may be made therein which are within the spirit of the invention and the scope of the appended claims.

What is claimed is:

1. A fluorescent conjugate comprising a biologically active moiety selected from the group consisting of a DNA probe, an antigen, an antibody, a hapten and an Fab fragment which is attached to a dye moiety by a substantially achromophoric divalent linking moiety, said dye moiety represented by the formula:

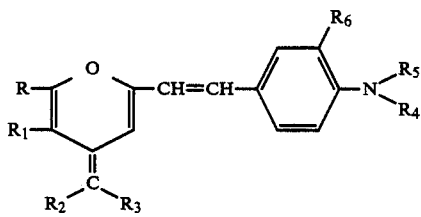

wherein R is alkyl having from 1 to 6 carbon atoms or a hydrophilic group; $R_1$ is hydrogen; or when R and $R_1$ are taken together they represent the carbon atoms necessary to form a fused benz ring;

$R_2$ and $R_3$ are each independently —CN, $COR_7$, $COOR_8$ or phenyl substituted with —CN, $COR_7$, $COOR_8$, or when $R_2$ and $R_3$ are taken together with the carbon atom to which they are attached they represent a group represented by

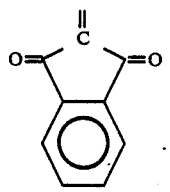

$R_4$ and $R_5$ are each independently alkyl having from 1 to 6 carbon atoms or a hydrophilic group; or $R_5$ when taken together with $R_6$ is —$(CH_2—)_2$;

$R_6$ is hydrogen;

$R_7$ is alkyl having from 1 to 6 carbon atoms or phenyl and;

$R_8$ is alkyl having from 1 to 6 carbon atoms, phenyl or a hydrophilic group;

provided that at least one of R, $R_4$, $R_5$ or $R_8$ is a hydrophilic group and wherein said biologically active moiety is attached to said dye moiety through any of the positions occupied by R, $R_2$, $R_3$, $R_4$ or $R_5$.

2. A conjugate as defined in claim 1 wherein said biologically active moiety is selected from the group consisting of an antigen, an antibody and an Fab fragment.

3. A conjugate as defined in claim 1 wherein said hydrophilic group is selected from the group consisting of carboxylic acids, polyethers, polyalcohols, amines, sulfonic acids, phosphonic acids, phosphonic esters, phosphates, phosphate esters, phosphinic acids, boronic acids and borinic acids.

4. A conjugate as defined in claim 3 wherein said hydrophilic group is selected from the group consisting of carboxylic acids, polyethers, polyalcohols, phosphonic acids and phosphonic esters.

5. An assay element adapted to receive a sample of a biological fluid and to provide a detectable signal as a function of the presence of an analyte in said fluid comprising a reagent layer including a fluorescent conjugate as defined in claim 1.

6. The assay element as defined in claim 5 wherein said biologically active moiety is selected from the group consisting of an antigen, an antibody and an Fab fragment.

7. The assay element as defined in claim 5 wherein said hydrophilic group is selected from the group consisting of carboxylic acids, polyethers, polyalcohols, amines, sulfonic acids, phosphonic acids, phosphonic esters, phosphates, phosphate esters, phosphinic acids, boronic acids and borinic acids.

8. The assay element as defined in claim 7 wherein said hydrophilic group is selected from the group consisting of carboxylic acids, polyethers, polyalcohols, phosphonic acids and phosphonic esters.

9. In a cell staining, fluorescence-activated cell sorting or a diagnostic assay method employing a fluorescent conjugate wherein a fluorescent labeled conjugate is brought together with an analyte with which it can take part in an immunological reaction and fluorescence is detected in relation to said reaction, the improvement comprising employing the fluorescent conjugate of claim 1.

10. A method as defined in claim 9, wherein said method is fluorescent activated cell sorting.

11. A method as defined in claim 9 wherein said method is a diagnostic assay employing a fluorescent conjugate.

12. The method as defined in claim 9 wherein in said conjugate said hydrophilic group is selected from the group consisting of carboxylic acids, polyethers, polyalcohols, amines, sulfonic acids, phosphonic acids, phosphonic esters, phosphates, phosphate esters, phosphinic acids, boronic acids and borinic acids.

* * * * *